US006417214B1

(12) United States Patent
Ullrich et al.

(10) Patent No.: US 6,417,214 B1
(45) Date of Patent: Jul. 9, 2002

(54) 3,3-SUBSTITUTED INDOLINE DERIVATIVES

(75) Inventors: John W. Ullrich, Exton; Andrew Fensome, Wayne, both of PA (US); Jay E. Wrobel, Lawrenceville, NJ (US); Lin Zhi, San Diego, CA (US); Todd K. Jones, Solana Beach, CA (US); James P. Edwards, San Diego, CA (US); Christopher M. Tegley, Thousand Oaks, CA (US)

(73) Assignees: Wyeth, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,352

(22) Filed: Apr. 19, 2000

Related U.S. Application Data
(60) Provisional application No. 60/183,061, filed on May 4, 1999.

(51) Int. Cl.⁷ .................. A61K 31/42; A61K 31/47; C07D 215/38; C07D 401/00; C07D 413/00
(52) U.S. Cl. .................. 514/378; 514/278; 514/314; 514/339; 546/159; 546/278.1; 548/245
(58) Field of Search ................ 514/278, 339, 514/314, 378; 546/278.1, 159; 548/245

(56) References Cited

U.S. PATENT DOCUMENTS

| | | | |
|---|---|---|---|
| 3,635,964 A | 1/1972 | Skorcz et al. | 260/247.1 |
| 3,917,592 A | 11/1975 | Kobzina | 260/244 |
| 4,093,730 A | 6/1978 | Butti | 424/270 |
| 4,258,185 A | 3/1981 | Nakao | 514/213 |
| 4,440,785 A | 4/1984 | Walsh | 424/317 |
| 4,666,913 A | 5/1987 | Kubla et al. | 514/259 |
| 4,670,566 A | 6/1987 | Walsh | 548/485 |
| 4,721,721 A | 1/1988 | Kuhla | 514/312 |
| 4,822,794 A | 4/1989 | Spada | 514/230 |
| 4,831,027 A | 5/1989 | Narr et al. | 514/212 |
| 4,853,473 A | 8/1989 | Fischer et al. | 549/326 |
| 4,916,128 A | 4/1990 | Jonas | 544/114 |
| 5,007,952 A | 4/1991 | Kume et al. | 71/73 |
| 5,171,851 A | 12/1992 | Kim et al. | 544/50 |
| 5,414,088 A | 5/1995 | Von Der Saal et al. | 546/158 |
| 5,453,516 A | 9/1995 | Fischer et al. | 548/543 |

(List continued on next page.)

FOREIGN PATENT DOCUMENTS

| | | |
|---|---|---|
| DE | 3633861 | 4/1988 |
| DE | 43 30 234 | 3/1995 |
| DE | 43 44 463 | 6/1995 |
| EP | 022317 | 1/1981 |
| EP | 0 208 510 | 1/1987 |
| EP | 311135 | 4/1989 |
| EP | 385850 | 9/1990 |

(List continued on next page.)

OTHER PUBLICATIONS

R.M. Evans, "The Steroid and Thyroid Hormone Receptor Superfamily", *Science*, 240:889 (May 13, 1988).
A. Ulmann et al., "Clinical Uses of Mifepristone (MFP)", *Ann. N.Y. Acad. Sci.*, 261:248 (Jun. 12, 1995).
R. Kekkonen et al., "Sequential Regiment of the Antiprogesterone RU486 and Synthetic Progestin for Contraception", *Fertility and Sterility*, 60(4):610 (Oct. 1993).
K. Horwitz et al., "Progestin, Progesterone Receptors, and Breast Cancer", "Horm. Cancer", publisher: Birkhaeuser, Boston, Mass., ed, Vedeckis, p. 283–306 (1996) abstract only.
A. A. Murphy et al., "Regression of Uterine Leiomyomata in Response to the Antiprogesterone RU 486", *J. Clin. Endo. Metab.*, 76(2):513 (Feb. 1993).
L. M. Kettel et al., "Endocrine Responses to Long–Term Administration of the Antiprogesterone RU486 in Patients with Pelvic Endometriosis", *Fertility and Sterility*, 56(3):402 (Sep. 1991).

(List continued on next page.)

*Primary Examiner*—Mukund J. Shah
*Assistant Examiner*—Tamthom N Truong
(74) *Attorney, Agent, or Firm*—Howson & Howson

(57) ABSTRACT

This invention provides compounds of the formula 1:

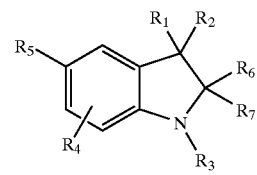

wherein:
$R_1$ and $R_2$ are chosen independently from each other from H, OH; OAc; alkylaryl; alkylheteroaryl; 1-propynyl; 3-propynyl; and optionally substituted alkyl, O(alkyl); aryl; or heteroaryl groups; or $R_1$ and $R_2$ are joined to form a ring comprising —$CH_2(CH_2)_nCH_2$— where $n=0-5$; —$CH_2CH_2CMe_2CH_2CH_2$—; —$O(CH_2)_mCH_2$— where $m=1-4$; $O(CH_2)_pO$— where $p=1-4$; —$CH_2CH_2OCH_2CH_2$—; —$CH_2CH_2N(H$ or alkyl$)CH_2CH_2$—;
or $R_1$ and $R_2$ together comprise a double bond to $CMe_2$; C(cycloalkyl), O, or C(cycloether);
$R_3$ is H, OH, $NH_2$, $COR^A$, or optionally substituted alkenyl or alkynyl groups;
$R^A$=H or optionally substituted alkyl, alkoxy, or aminoalkyl groups;
$R_4$=H, halo, CN, $NH_2$, or optionally substituted alkyl, alkoxy, or aminoalkyl;
$R_5$ is selected from optionally substituted benzene ring; a five or six membered heterocyclic ring; a 4 or 7-substituted indole or a substituted benzothiophene; or pharmaceutically acceptable salt thereof, as well as pharmaceutical compositions and methods of using the compounds as progesterone receptor antagonists.

15 Claims, No Drawings

U.S. PATENT DOCUMENTS

| | | | |
|---|---|---|---|
| 5,475,020 A | 12/1995 | Johnson et al. | 548/466 |
| 5,521,166 A | 5/1996 | Grubb | 514/170 |
| 5,681,817 A | 10/1997 | Hodgen et al. | 514/12 |
| 5,688,808 A | 11/1997 | Jones et al. | 514/285 |
| 5,688,810 A | 11/1997 | Jones et al. | 514/311 |
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |
| 5,696,133 A | 12/1997 | Pooley et al. | 514/314 |
| 5,719,136 A | 2/1998 | Chwalisz et al. | 514/170 |
| 5,733,902 A | 3/1998 | Schneider | 514/177 |
| 5,808,139 A | 9/1998 | Pathirana | 560/138 |
| 5,874,430 A | 2/1999 | Christ | 514/229.8 |
| 6,077,840 A | 6/2000 | Kurihara | 514/232.8 |

FOREIGN PATENT DOCUMENTS

| | | |
|---|---|---|
| EP | 483077 | 9/1991 |
| EP | 454330 | 10/1991 |
| EP | 0 535 529 | 9/1992 |
| EP | 510235 | 10/1992 |
| EP | 947 507 | 10/1999 |
| EP | 978 279 | 2/2000 |
| JP | 63112584 | 5/1988 |
| WO | WO 86/03749 | 7/1986 |
| WO | WO 91/04974 | 4/1991 |
| WO | WO 91/06545 | 5/1991 |
| WO | WO 93/12085 | 6/1993 |
| WO | WO 94/14434 | 7/1994 |
| WO | WO 94/29272 | 12/1994 |
| WO | WO 95/11013 | 4/1995 |
| WO | WO 95/20389 | 8/1995 |
| WO | WO 95/20972 | 8/1995 |
| WO | WO 95/33746 | 12/1995 |
| WO | WO 96/15794 | 5/1996 |
| WO | WO 96/19458 | 6/1996 |
| WO | WO 96/19997 | 7/1996 |
| WO | WO 97/13767 | 4/1997 |
| WO | WO 97/49407 | 12/1997 |
| WO | WO 98/14436 | 4/1998 |
| WO | WO 98/27069 | 6/1998 |
| WO | WO 98/55116 | 12/1998 |
| WO | WO 99/10325 | 3/1999 |
| WO | WO 99/11264 | 3/1999 |
| WO | WO 99/15500 | 4/1999 |
| WO | WO 99/44608 | 9/1999 |

OTHER PUBLICATIONS

H. Michna et al., "Differentiation Therapy with Progesterone Antagonists", *Ann. N.Y. Acad. Sci.*, 761:224 (Jun. 1995).

L. Zhi et al., "5–Aryl–1,2–Dihydrochromeno[3,4–f]quinolines: A Novel Class of Nonsteroidal Human Progesterone Receptor Agonists", *J. Med. Chem.*, 41(3):291 (Oct. 22, 1998).

D. W. Combs et al., "Nonsteroidal Progesterone Receptor Ligands. 2, High–Affinity Ligands with Selectivity for Bone Cell Progesterone Receptors", *J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al., "Preparation, Testing, and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor: Imidazo [4,5–b]pyridin–2(3H)–ones and Thiazolo[4,5–b] pyridin–2(3H)–ones and Their Analogs", *J. Med. Chem.*, 37:248 (Jan. 21, 1994).

A. Andreani et al., "Potential Antitumor Agents XVII (1). Cytotoxic Agents from Indole Derivatives and Their Intermediates", *Acta. Pharm. Nord.*, 2(6):407 (1990).

Sakata et al., "Silver Halide Photographic Materials Useful for Platemaking", *Chemical Abstracts*, 123:301431 (1993).

P. Pflegel et al., "Polarografie con 7–Chlor–5–phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovariectomized Rats", *Bone*, 17(1):21 (Jul. 1995).

E. V. Gromachevskaya et al., "Studies of 4H–3, 1–Benzoxazines", *Chem. Heterocycl. Cmpds.* 33(10):1209–1214 (1997).

D. Chiarino et al., "2, 1–Benzisothiazoline 2,2–Dioxide and Derivatives", *J. Heterocycl. Chem.*, 23(6):1645–1649 (Nov.–Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(O–Aminophenyl)cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothiazinylpyridazinones", *J. Med. Chem.*, 35:172–176 (Jan. 1992).

Kurihari et al., "Synthesis of (±)–PF1092A, B, and C; New Nonsteroidal Progesterone Receptor Ligands", *J. Antibiotics*, 50(4):360 (Apr. 1997).

A. Kende et al., "Regioselective C–3 Alkylation of Oxindole Dianion", *Synth. Commun. 12*(1):1 (1982).

T. Tucker et al., "Synthesis of a Series of 4–(Arylethylnyl)–6–Chloro–4–Cyclopropyl–3, 4–dihydroquinazolin–2(1H)–ones as Novel–Nucleoside HIV–1 Reverse Transcriptase Inhibitors", *J. Med. Chem.*, 37:2347–2444 (Jul. 22, 1994).

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Substituents", *J. Med. Chem.*, 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850.

Derwent WPI abstract, F. Arndt et al., "New Heterocycle substituted Benzo–Fused Azine and Azole Derivatives—Useful as Selective Herbicides for Pre or Post–Emergence Application", EP 311135.

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

Mamaev, V.P., et al., "Synthesis of 4H–Thieno [3,2–B] Pyrrol–5(6H)–One" Bulletin of the Academy of Sciences on the USSR Division of Chemical Science, US, Consultants Bureau. New York. vol. 9, p. 1549–1553, 1966.

Derwent WPI Abstract, Chwalisz, K., et al. "Female Contraceptive Method Comprises Gestation Treatment with Intermittent Progesterone Antagonist Administration.", DE 4,330,234.

Derwent WPI Abstract, Chwalisz, K., et al. "Contraceptive Pack for Implantation Inhibition—Contains Competitive Progesterone Antagonist and Gestagen for Sequential Oral Administration.", DE 4,344,463.

Kolasa, K., et al., "Preliminary Pharmacological Studies of the Central Action of Phenyl and Piperidinomethyl Derivatives of 2–Benzoxazolone." *Chemical Abstracts*, vol. 99, No. 1, Abst. No. 157a, Jul. 4, 1983.

Meanwell N.A., et al., "Regiospecific Functionalization of 1,3–dihydro–2H–Benzimidazol–2–One and Structurally Related Cyclic Urea Derivatives" *J. Organic Chem.*, 60(6): 1565–82 (Mar. 24, 1995).

Singh, B., et al., "An Efficient and Novel Synthesis of Fused Thiazol–2(3H)–ones" *Heterocycles*, 36(1): 133–134, p. 136, compounds 16a, 18a, Jan. 1993.

Vernin, G., et al., "Etude Dans 1a Serie des Radicaux Heterocycliques. Partie XV. Decomposition aprotique de l'amino–6–ethyl–2–benzothiazole dans des substrats aromatiques et heteroaromatiques: preparation des mesityl–6– et furyl–6–ethyl–2–benzothiazoles des sels quaternaires et des spiropyrannes correspondants" *Helvetica Chimica Acta*, 62(1/3):21–30 Jan. 24, 1979.

3,3-SUBSTITUTED INDOLINE DERIVATIVES

CROSS-REFERENCE TO RELATED APPLICATION

This application claims the benefit of the priority of U.S. Provisional Patent Application No. 60/183,061, filed May 4, 1999.

FIELD OF THE INVENTION

This invention relates to compounds which are antagonists of the progesterone receptor, their preparation and utility.

BACKGROUND OF THE INVENTION

Intracellular receptors (IR) form a class of structurally related gene regulators known as "ligand dependent transcription factors" (R. M. Evans, *Science*, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound which inhibits the effect of the hormone is an antagonist.

PR antagonists may be used in contraception. In this context they may be administered alone (Ulmann, et al, *Ann. N.Y. Acad. Sci.*, 261, 248, 1995), in combination with a PR agonist (Kekkonen, et al, *Fertility and Sterility*, 60, 610, 1993) or in combination with a partial ER antagonist such as tamoxifen (WO 96/19997, published Jul. 4, 1996).

PR antagonists may also be useful for the treatment of hormone dependent breast cancers (Horwitz, et al, *Horm. Cancer,* 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, *J. Clin. Endo. Metab.*, 76, 513, 1993) and endometriosis (Kettel, et al, *Fertility and Sterility,* 56, 402, 1991). PR antagonists may further be useful in hormone replacement therapy for post menopausal patients in combination with a partial ER antagonist such as tamoxifen (U.S. Pat. No. 5,719,136). PR antagonists, such as mifepristone and onapristone, have been shown to be effective in a model of hormone dependent prostate cancer, which may indicate their utility in the treatment of this condition in men (Michna, et al, *Ann. N.Y. Acad. Sci.*, 761, 224, 1995).

Jones, et al, (U.S. Pat. No. 5,688,810) describe the PR antagonist dihydroquinoline A.

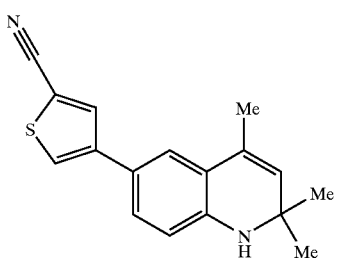

Jones, et al, described the enol ether B (U.S. Pat. No. 5,693,646) as a PR ligand.

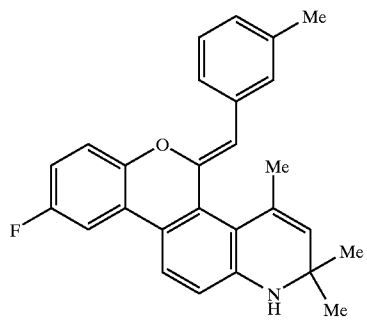

Jones, et al, described compound C (U.S. Pat. No. 5,696,127) as a PR ligand.

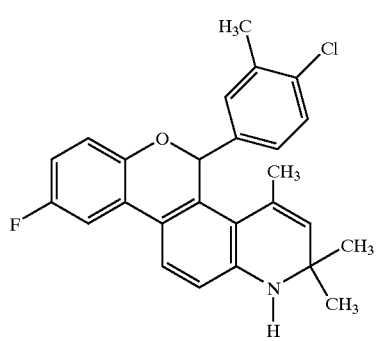

Zhi, et al, described lactones D, E and F as PR antagonists (J. Med. Chem., 41, 291, 1998).

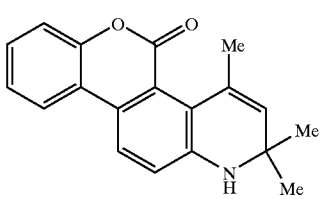

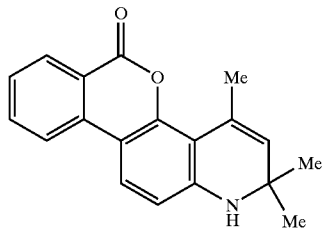

E

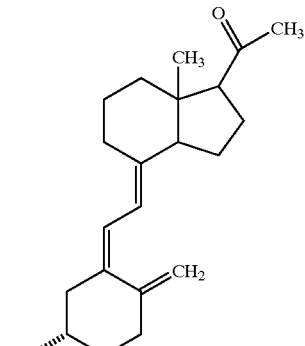

I

Hamann, et al, described the PR antagonist J (*Ann. N.Y. Acad. Sci.,* 761, 383, 1995).

Zhi, et al, described the ether G as a PR antagonist (*J. Med. Chem.,* 41, 291, 1998).

F

J

Chen, et at, described the PR antagonist K (Chen, et al, POI-37, 16th Int. Cong. Het. Chem., Montana, 1997).

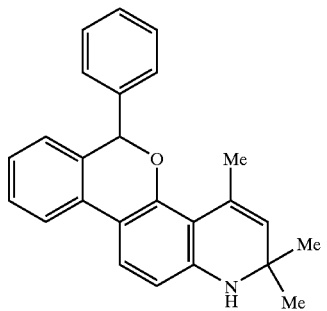

G

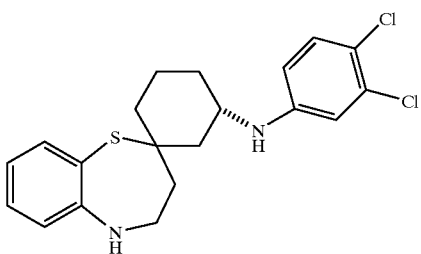

K

Combs, et al., disclosed the amide H as a ligand for the PR (*J. Med. Chem.,* 38, 4880, 1995).

Kurihari, et. at., described the PR ligand L (*J. Antibiotics,* 50, 360, 1997).

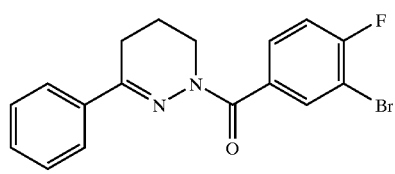

H

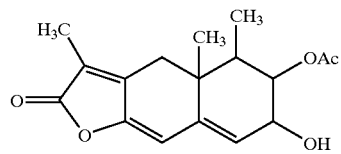

L

Perlman, et. al., described the vitamin D analog I as a PR ligand (*Tet. Letters,* 35, 2295, 1994).

Elliott (Smith Kline Beecham) claimed the generic indoline M as potential endothelin receptor antagonists (WO 94/14434). The patent does not claim indolines and lacks the appropriate 5-aryl substitution, i.e. CN and $NO_2$.

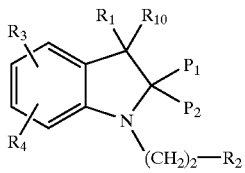

M $R_1$, $R_{10}$, $P_1$ and $P_2$ = H, 1–8 C alkyl, Ph
n = 0
$R_3$ = H
$R_2$ = H
$R_4$ = Ar(substituted)

wherein: $R_4$=H, Ar, $R_{11}$, OH, 1–5 C alkoxy (opt. substd. by OH, OMe or halogen), —S(O)$_q$R$_{11}$, N(R$_6$)$_2$, XR$_{11}$, halogen or NHCOR$_6$; X=(CH$_2$)$_n$, O, NR$_6$ or S(O)$_q$; n=0–6; q=0–2; R$_6$=H or 1–4 C alkyl; R$_{11}$=1–8 C alkyl, 2–8 C alkenyl or 2–8 C alkynyl (all optionally substituted); Ar=(i) opt. substd. phenyl or benzo-fused gp. of (a) or (b); or (ii) napthyl, indoyl, pyridyl, thienyl, oxazolindyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, pyrrolyl or pyrimidyl, all opt. substd. by one or more $R_1$ or $R_2$ groups.

(a)

(b)

A = CO or (C(R$_6$)$_2$)$_m$
B = CH$_2$ or O

DESCRIPTION OF THE INVENTION

The compounds of this invention have been shown to act as competitive inhibitors of progesterone binding to the PR and act as antagonists in functional models, either/or in-vitro and in-vivo. These compounds may be used for contraception, in the treatment and/or prevention of fibroids, including uterine fibroids, endometriosis, breast, uterine, ovarian and prostate cancer, and post menopausal hormone replacement therapy. This invention also particularly relates to methods of using these compounds in the induction of contraception and the treatment and/or prevention of benign and malignant neoplastic disease. Such diseases may include, without limitation, benign prostatic hypertrophy, carcinomas and adenocarcinomas of the endometrium, ovary, breast, colon, prostate, pituitary, meningioma and other hormone-dependent tumors.

Compounds of this invention include compounds of the formula I:

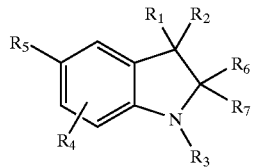

I wherein:
$R_1$ and $R_2$ are chosen independently from H, alkyl, substituted alkyl; OH; O(alkyl); O(substituted alkyl); OAc; aryl; optionally substituted aryl; heteroaryl; optionally substituted heteroaryl; alkylaryl; alkylheteroaryl; 1-propynyl; or 3-propynyl;

or $R_1$ and $R_2$ are joined to form a ring comprising one of the following: —CH$_2$(CH$_2$)$_n$CH$_2$—; —CH$_2$CH$_2$CMe$_2$CH$_2$CH$_2$—; —O(CH$_2$)$_m$CH$_2$—; O(CH$_2$)$_p$O—; —CH$_2$CH$_2$OCH$_2$CH$_2$—; —CH$_2$CH$_2$N(H or alkyl)CH$_2$CH$_2$—;

n is an integer from 0 to 5;
m is an integer from 1 to 4;
p is an integer from 1 to 4;

or $R_1$ and $R_2$ together comprise a double bond to =C(CH$_3$)$_2$; =C(C$_3$–C$_6$ cycloalkyl), =O, or =C(cycloether), wherein cycloether is selected from tetrahydrofuranyl or hexahydropyranyl;

$R_3$ is H, OH, NH$_2$, C$_1$ to C$_6$ alkyl, substituted C$_1$ to C$_6$ alkyl, C$_3$ to C$_6$ alkenyl, alkynyl or substituted alkynyl, or COR$^A$;

$R^A$=H, C$_1$ to C$_3$ alkyl, substituted C$_1$ to C$_3$ alkyl, C$_1$ to C$_3$ alkoxy, substituted C$_1$ to C$_3$ alkoxy, C$_1$ to C$_3$ aminoalkyl, or substituted C$_1$ to C$_3$ aminoalkyl;

$R_4$=H, halogen, CN, NH$_2$, C$_1$ to C$_6$ alkyl, substituted C$_1$ to C$_6$ alkyl, C$_1$ to C$_6$ alkoxy, substituted C$_1$ to C$_6$ alkoxy, C$_1$ to C$_6$ aminoalkyl, or substituted C$_1$ to C$_6$ aminoalkyl;

$R_5$ is selected from the groups a), b) or c):
a) $R_5$ is a trisubstituted benzene ring containing the substituents X, Y and Z as shown below:

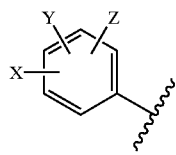

X is selected from halogen, OH, CN, C$_1$ to C$_3$ alkyl, substituted C$_1$ to C$_3$ alkyl, C$_1$ to C$_3$ alkoxy, substituted C$_1$ to C$_3$ alkoxy, C, to C$_3$ thioalkyl, substituted C$_1$ to C$_3$ thioalkyl, S(O)alkyl, S(O)$_2$alkyl, C$_1$ to C$_3$ aminoalkyl, substituted C$_1$ to C$_3$ aminoalkyl, NO$_2$, C$_1$ to C$_3$ perfluoroalkyl, 5 or 6 membered heterocyclic ring containing 1 to 3 heteroatoms, COR$^B$, OCOR$^B$, or NR$^C$COR$^B$;

$R^B$ is H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;

$R^C$ is H, C$_1$ to C$_3$ alkyl, or substituted C$_1$ to C$_3$ alkyl:
Y and Z are independent substituents taken from the group including H, halogen, CN, NO$_2$, C$_1$ to C$_3$ alkoxy, C$_1$ to C$_3$ alkyl, or C$_1$ to C$_3$ thioalkyl; or b) $R_5$ is a five or six membered ring with 1, 2, or 3 heteroatoms from the group including O, S, SO, SO$_2$ or $NR_6$ and containing one or two independent substituents from the group including H, halogen, CN, $NO_2$ and $C_1$ to $C_3$ alkyl, $C_1$ to $C_3$ alkoxy, $C_1$ to $C_3$ aminoalkyl, $COR^D$, or $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

$R_6$ is H or $C_1$ to $C_3$ alkyl; or c) $R^5$ is an indol-4-yl, indol-7-yl or benzo-2-thiophene moiety, the moiety being optionally substituted by from 1 to 3 substituents selected from halogen, lower alkyl, CN, $NO_2$, lower alkoxy, or $CF_3$; wherein $R_6$ and $R_7$ are independently chosen from H, methyl, ethyl, propyl, butyl, iso-propyl, iso-butyl, cyclohexyl, aryl, substituted aryl, heteroaryl, or substituted heteroaryl;

or pharmaceutically acceptable salt thereof.

A preferred set of compounds of this invention is depicted by structure II:

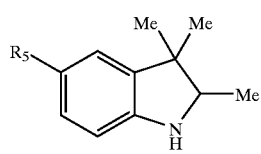

wherein:

$R_5$ is a disubstituted benzene ring containing the substituents X, and Y as shown below:

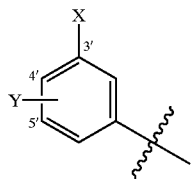

X is selected from halogen, CN, $C_1$ to $C_3$ alkoxy, $C_1$ to $C_3$ alkyl, $NO_2$, $C_1$ to $C_3$ perfluoroalkyl, 5-membered heterocyclic ring containing 1 to 3 heteroatoms, or $C_1$ to $C_3$ thioalkoxy;

Y is a substituent on the 4' or 5' position selected from H, halogen, CN, $NO_2$, $C_1$ to $C_3$ alkoxy, $C_1$ to $C_4$ alkyl, or $C_1$ to $C_3$ thioalkyl; or $R_5$ is a five membered ring having the structure:

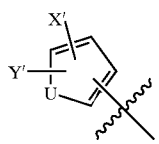

U is O, S, or $NR_6$, $R_6$ is H, or $C_1$ to $C_3$ alkyl, or $C_1$ to $C_4$ $CO_2$ alkyl;

X' is selected from halogen, CN, $NO_2$, $C_1$ to $C_3$ alkyl or $C_1$ to $C_3$ alkoxy;

Y' is selected from the group H, F, CN, $NO_2$ or $C_1$ to $C_4$ alkyl; or $R_5$ is a six-membered ring with the structure:

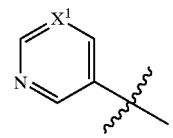

$X^1$ is N or $CX^2$;

$X^2$ is halogen, CN or $NO_2$;

or pharmaceutically acceptable salt thereof.

The compounds of this invention may contain an asymmetric carbon atom and some of the compounds of this invention may contain one or more asymmetric centers and may thus give rise to optical isomers and diastereomers. While shown without respect to stereochemistry in Formulas I and II, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having 1 to 8 carbon atoms, preferably 1 to 6 carbon atoms; "alkenyl" is intended to include both straight- and branched-chain alkyl group with 1 or 2 carbon-carbon double bonds and containing 2 to 8 carbon atoms, preferably 2 to 6 carbon atoms; "alkynyl" group is intended to cover both straight- and branched-chain alkyl group with at least 1 or 2 carbon-carbon triple bonds and containing 2 to 8 carbon atoms, preferably 2 to 6 carbon atoms.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but not limited to phenyl, naphthyl, biphenyl, anthryl, tetrahydronaphthyl, phenanthryl.

The term "substituted aryl" refers to an aryl as just defined having 1 to 4 substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having 1 to 4 substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "thioalkyl" is used herein to refer to the SR group, where R is alkyl or substituted alkyl, containing 1 to 8 carbon atoms. The term "alkoxy" refers to the OR group, where R is alkyl or substituted alkyl, containing 1 to 8 carbon atoms. The term "aryloxy" refers to the OR group, where R is aryl or substituted aryl, as defined above. The term "alkylcarbonyl" refers to the RCO group, where R is alkyl or substituted alkyl, containing 1 to 8 carbon atoms, preferably 1 to 6 carbon atoms. The term "alkylcarboxy" indicates the COOR group, where R is alkyl or substituted alkyl, containing 1 to 8 carbon atoms, preferably 1 to 6 carbon atoms. The term "aminoalkyl" refers to both secondary and tertiary amines wherein the alkyl or substituted alkyl groups, containing 1 to 8 carbon atoms, which may be either the same or different and the point of attachment is on the nitrogen atom. The term "halogen" refers to Cl, Br, F, or I.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

This invention includes pharmaceutical compositions comprising one or more compounds of this invention and a pharmaceutically acceptable carrier or excipient. The invention also includes methods of treatment which comprise administering to a mammal a pharmaceutically effective amount of one or more compounds as described above as antagonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors, particularly progesterone-related tumors. Additional uses of the present progesterone receptor antagonists include the synchronization of the estrus in livestock.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The compounds of this invention can be prepared by the procedures outlined in the Schemes illustrated below:

Typically the compounds of this invention are prepared in a convergent manner as shown is Scheme 1, by a suitable coupling reaction. For example, a palladium mediated coupling of an aryl halide with an aryl boronic acid provides the desired bi-aryl substituted target. The choice of the aryl halide-aryl boronic acid combination is established experimentally.

Scheme 1

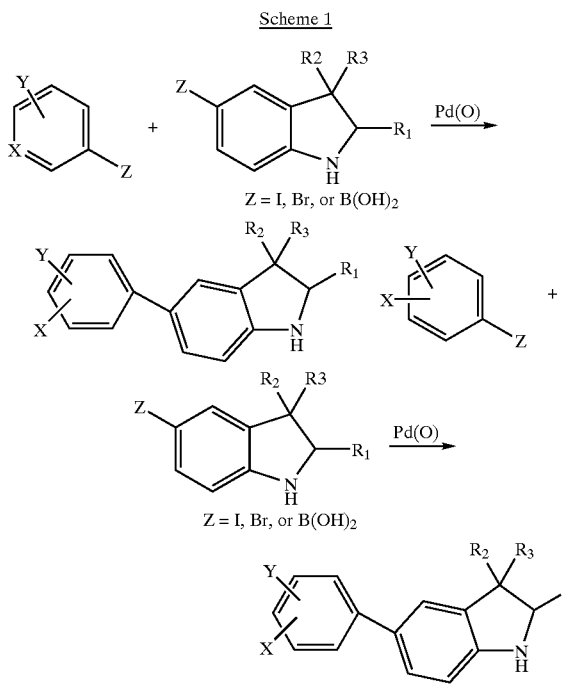

As outlined in Scheme 2, the "right side" of the compounds of this invention may be prepared by following the procedure described in Letcher, R. M. et. al., *J. Chem. Soc. Perkin Trans.*, 1: 939–944, 1993.

Scheme 2

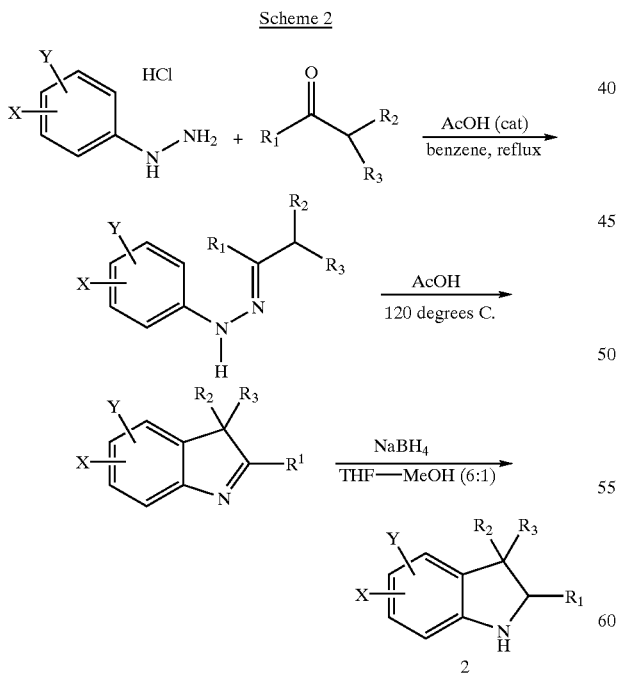

As an example, the right side template, 2, is prepared by condensing an appropriately substituted phenyl hydrazine and a suitable ketone to give the corresponding hydrazone. This material is cyclized to an imine in refluxing acetic acid and then reduced to the desired indoline template 2. Examples 1–7 and 10–20 were prepared by this route using the appropriate ketone.

Alternatively the right side template may be prepared as outlined in Scheme 3. The commercially available oxindole is di-alkylated at C-3 by using an appropriate base and the corresponding alkyl halide to give the 3,3-dialkyl-oxindole, 8, or the spiro-cyclic oxindole 9. These oxindoles are then brominated under standard conditions and the carbonyl group is reduced to the desired methylene using a hydride mediated reduction. The timing of the aryl coupling and the reduction of the 2-position carbonyl are established experimentally.

Scheme 3

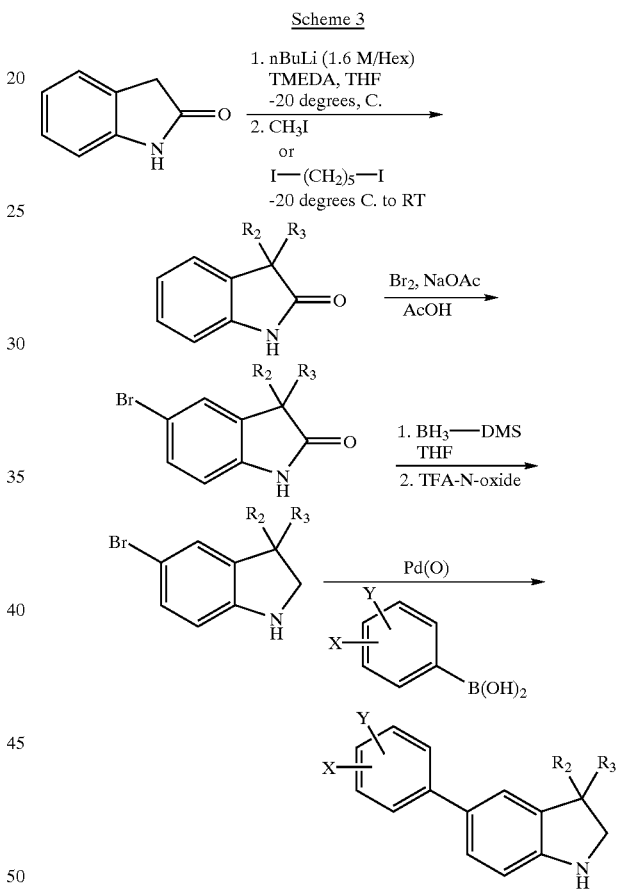

The right side templates are coupled with an appropriate aryl boronic acid using an appropriate palladium (0) catalyst, Scheme 4. For example compound 10 is coupled under standard Suzuki conditions with an appropriately substituted aryl-boronic acid to afford compound 11.

Scheme 4

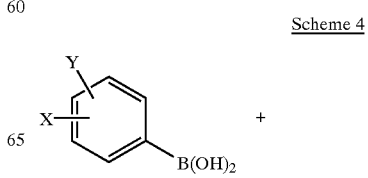

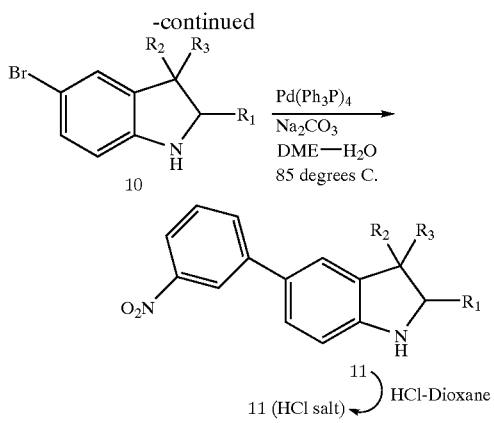

The compounds of this invention, are stable semi-solids and are conveniently converted into their corresponding salts by treatment with acid. Example 1, compound 11 ($R_1$=$R_2$=$R_3$=Me), when treated with HCl in dioxane affords the HCl salt (Example 2) as a white solid. The racemic indolines can be separated into their enantiomers by Chiral HPLC, to provide the individual enantiomers in >98% EE.

This invention may be further understood by the following non-limiting examples.

EXAMPLE 1

2,3,3-Trimethyl-5-(3-nitro-phenyl)-2,3-dihydro-1H-indole 5-Bromo-2,3,3-trimethyl-2,3-dihydro-1H-indole This compound was prepared by the procedure of Letcher, R. M. et. al., *J. Chem. Soc. Perkin Trans.*, 1: 939–944, 1993.

To a solution of 4-bromo-phenyl hydrazine hydrochloride (2.59 g, 11.6 mmol) and 3-methyl-2-butanone (1.0 g, 11.6 mmol) in 20 mL benzene was added acetic acid (catalytic amount) and the resulting solution was refluxed with azeotropic removal of $H_2O$ for 14 h. The reaction mixture cooled to room temperature and concentrated. The resulting semi-solid was extracted in acetic acid and refluxed for 12 hours. The reaction mixture was cooled to room temperature and concentrated. The semi-solid residue was extracted in ether and neutralized with $K_2CO_3$. The ether layer was dried and concentrated. The resulting solid imine was dissolved in THF-MeOH (6:1), cooled to 0° C. and sodium borohydride (0.5 g, 13.2 mmol) was added. The solution was allowed to warm to room temperature and stirred for 0.5 hours. The reaction mixture was poured into 15% aqueous HCl and then made basic with $K_2CO_3$. The organic layer was separated, washed with brine, dried ($Na_2SO_4$), and concentrated. The crude product was purified by column chromatography ($SiO_2$, hexane-ethyl acetate 9:1). The product was isolated as an orange liquid (2.1 g, 75%): $^1$H-NMR (CDCl$_3$) δ1.03 (s, 3H), 1.15 (d, J=6.6 Hz, 3H), 1.25 (s, 3H), 3.50 (q, J=6.6 Hz, 1H), 3.70 (br. s, 1H), 6.45 (d, J=8.7 Hz, 1H), 7.09 (m, 2H); $^{13}$C-NMR (CDCl$_3$) δ15.10, 22.25, 26.11 (q), 43.72 (s), 65.47 (d), 110.32 (s), 110.70, 125.47, 129.75 (d), 141.48, 148.33 (s); MS (EI) m/z 240, 242 (M+H)$^+$.

A solution of 5-bromo-2,3,3-trimethyl-2,3-dihydro-1H-indole (0.5 g, 2.1 mmol) and tetrakis-(triphenylphosphine) palladium (0.14 g, 0.12 mmol) in dimethoxyethane (10 mL) was cycled under $N_2$-vacuum (4x) and then stirred under $N_2$ for 0.5 hours. To this mixture was then added 3-nitrophenylboronic acid (0.42 g, 2.5 mmol) followed by a solution of $Na_2CO_3$ (0.36 g, 3.4 mmol) in 5 mL water cycled under $N_2$-vacuum (3x). The solution was brought to reflux for 6 hours then cooled to room temperature, poured into water and extracted with EtOAc. The combined organic extracts were washed with water, brine, dried ($Na_2SO_4$), and evaporated. The residue was purified by column chromatography ($SiO_2$, methylenechloride:hexane 1:3) to afford the title compound (0.48 g, 82%) as an orange semi-solid: $^1$H NMR (CDCl$_3$) δ1.12 (s, 3H), 1.21 (d, J=6.6 Hz, 3H), 1.35 (s, 3H), 3.60 (q, J=6.6 Hz, 1H), 3.9 (br s, 1H), 6.69 (d, J=7.9 Hz, 1H), 7.28–7.29 (m, 2H), 7.32 (d, J=1.9 Hz, 1H), 7.53 (dd, J=7.9, 7.9 Hz, 1H), 7.85 (ddd, J=7.9, 2.0, 2.0 Hz, 1H), 8.07 (ddd, J=7.9, 2.0, 2.0 Hz, 1H), 8.08 (d, J=7.9 Hz, 1H), 8.39 (dd, J=2.0, 2.0 Hz, 1H); $^{13}$C-NMR (CDCl$_3$) δ15.27, 22.54, 26.39 (q), 43.53 (s), 65.57 (d), 109.48, 120.67, 121.04, 121.10, 126.58 (d), 129.15 (s), 129.53, 132.35 (d), 140.18, 143.64, 148.78, 150.11 (s); MS (EI) m/z 283 (M+H)$^+$.

EXAMPLE 2

2,3,3-Trimethyl-5-(3-nitro-phenyl)-2,3-dihydro-1H-indole Hydrochloride

A solution of 2,3,3-trimethyl-5-(3-nitro-phenyl)-2,3-dihydro-1H-indole (0.8 g, 2.79 mmol) in 20 mL of 1:1 ether:dioxane at room temperature was treated with 1.5 mL of a 4 M HCl/dioxane solution. The resulting solid was isolated by filtration and washed with hexane to afford the title compound (0.81 g, 90%) as a tan solid: m.p. 240–241°; $^1$H-NMR (CDCl$_3$) δ1.37 (s, 3H), 1.51 (s, 3H), 4.01 (d, J=6.5 Hz, 1H), 7.51 (s, 1H), 7.59 (d, J=7.3 Hz, 1H), 7.7 (dd, J=7.9, 7.9 Hz, 1H), 7.8 (d, J=7.9, Hz, 1H), 7.89 (d, J=7.7 Hz, 1H), 8.3 (dd, J=7.9, 1.8 Hz, 1H), 8.42 (s, 1H), 11.9 (br s. 2H); $^{13}$C-NMR (CDCl$_3$) δ; MS (EI) m/z 283 (M+H)$^+$.

EXAMPLE 3

(2-R or S)-2,3,3-Trimethyl-5-(3-nitro-phenyl)-2,3-dihydro-1H-indole and and

EXAMPLE 4

(2-S or R)-2,3,3-Trimethyl-5-(3-nitro-phenyl)-2,3-dihydro-1H-indole

A sample of racemic 2,3,3-trimethyl-5-(3-nitro-phenyl)-2,3-dihydro-1H-indole (25 mg), as prepared in example 2, was separated by a chiral preparative HPLC [column: Chiralcel OD, 4.6×250 mm, isocratic, 5:95 IPA:hexane, flow rate=1 mL/min; injection volume=5 μL; retention times: 3, 9.2 min and 4, 10.39 min.] to provide the enantiomers 3 and 4 as orange semi-solids. Chiral Analytical HPLC determined that the enantiomers had >99% EE. Examples 3 and 4 have spectral data identical to the racemic material, example 1: $^1$H-NMR (CDCl$_3$) δ1.12 (s, 3H), 1.21 (d, J=6.6 Hz, 3H), 1.35 (s, 3H), 3.60 (q, J=6.6 Hz, 1H), 3.9 (br s, 1H), 6.69 (d, J=7.9 Hz, 1H), 7.28–7.29 (m, 2H), 7.32 (d, J=1.9 Hz, 1H), 7.53 (dd, J=7.9, 7.9 Hz, 1H), 7.85 (ddd, J=7.9, 2.0, 2.0 Hz, 1H), 8.07 (ddd, J=7.9, 2.0, 2.0 Hz, 1H), 8.08 (d, J=7.9 Hz, 1H), 8.39 (dd, J=2.0, 2.0 Hz, 1H); MS (EI) m/z 283 (M+H)$^+$.

EXAMPLE 5

2,3,3-Diethyl-2-methyl-5-(3-nitro-phenyl)-2,3-dihydro-1H-indole

5-Bromo-3,3-diethyl-2-methyl-2,3-dihydro-1H-indole

This compound was prepared according to the procedure for Example 1 using 4-bromo-phenyl hydrazine hydrochloride (5.9 g, 26.3 mmol) and 3-ethyl-2-pentanone (3.0 g, 26.3 mmol). The subtitled compound (4.5 g) was obtained in 65% yield as a yellowish oil: $^1$H-NMR (CDCl$_3$) δ0.81 (t, J=7.4 Hz, 3H), 0.83 (t, J=7.4 Hz, 3H), 1.18 (d, J=6.5 Hz, 3H), 1.42 (dq, J=14.0, 7.4 Hz, 1H), 1.66 (dq, J=14.0, 7.4 Hz, 3H), 3.73 (q, J=6.5 Hz, 1H), 6.47 (d, J=8.2 Hz, 1H), 7.02 (d, J=2 Hz, 1H), 7.09 (dd, J=8.2, 2.0Hz, 1H); $^{13}$C-NMR (CDCl$_3$) δ10.46, 10.66, 17.70 (q), 26.5, 29.67 (t), 52.25 (s), 64.80 (d), 111.64 (s), 112.41, 129.07, 131.58 (d), 139.57, 151.04 (s); MS (EI) m/z 268, 270 (M+H)$^+$.

Using the standard coupling conditions given in Example 1 the title compound was prepared from 5-bromo-3,3-diethyl-2-methyl-2,3-dihydro-1H-indole (0.13 g, 0.45 mmol), tetrakis-(triphenylphosphine) palladium (0.05 g, 0.04 mmol) in dimethoxyethane (4 mL) with 3-nitrophenylboronic acid (0.09 g, 0.54 mmol) and sodium carbonate (0.15 g, 4.95 mmol) in 2 mL of water. The title compound (0.09 g, 65%) was obtained as a red brown glass: $^1$H NMR (CDCl$_3$) δ0.86 (dt, J=4.0, 4.0 Hz, 3H), 0.88 (dt, J=4.0, 4.0 Hz, 3H), 1.24 (d, J=6.6 Hz, 3H), 1.5 (dq, J=14.1, 7.3 Hz, 1H), 1.66–1.84 (m, 3H), 3.81 (q, J=6.6 Hz, 1H), 6.69 (d, J=8.0 Hz, 1H), 7.20 (d, J=1.9 Hz, 1H), 7.32 (dd, J=8.0, 1.9 Hz, 1H), 7.53 (dd, J=8.0, 8.0 Hz, 1H), 7.85 (dd, J=7.9, 1.1 Hz, 1H), 8.09 (dd, J=7.9, 1.1 Hz, 1H), 8.4 (dd, J=1.9 Hz, 1H); $^{13}$C-NMR (CDCl$_3$) δ8.99, 9.14, 16.24 (q), 24.87, 28.14 (t), 50.30 (s), 63.31 (d), 109.56, 120.80, 121.22, 123.19, 126.76 (d), 128.64 (s), 129.67, 132.55 (d), 136.5, 143.92, 148.95, 151.07 (s); MS (EI) m/z 310 (M)$^+$.

EXAMPLE 6

4a-Methyl-6-(3-nitro-phenyl)-2,3,4,4a,9,9a-hexahydro-1H-carbazole

6-Bromo-4a-methyl-2,3,4,4a,9,9a-hexahydro-1H-carbazole

This compound was prepared by the procedure of Example 1 using 4-bromo-phenyl hydrazine hydrochloride (2.0 g, 8.95 mmol) and 2-methylcyclohexanone (1.0 g, 8.95 mmol). The subtitled compound (1.5 g, 65%) was obtained as a yellow oil: $^1$H NMR (CDCl$_3$) δ1.26 (s, 3H), 1.38–1.46 (m, 4H), 1.56–1.68 (m, 4H), 3.4 (t, J=4.4 Hz, 1H), 3.6 (br s, 1H), 6.53 (d, J=8 Hz, 1H), 7.08 (d, J=2.0 Hz, 1H), 7.09 (dd, J=8.0, 2.0 Hz, 1H); $^{13}$C-NMR (CDCl$_3$) δ21.45, 21.87 (t), 23.96 (q), 27.92, 35.32 (t), 43.56 (s), 66.65 (d), 110.73 (s), 111.88, 125.25, 129.99 (d), 142.17, 149.03 (s); MS (EI) m/z 268, 270 (M+H)$^+$.

Using the standard coupling conditions given in Example 1, the title compound was prepared using 6-bromo-4a-methyl-2,3,4,4a,9,9a-hexahydro-1H-carbazole (1.6 g, 6.0 mmol), tetrakis(triphenylphosphine) palladium (0.4 g, 0.35 mmol) in dimethoxyethane (30 mL) with 3-nitrophenylboronic acid (1.2 g, 7.2 mmol) and sodium carbonate (1.9 g, 18 mmol) in 10 mL water. The pure product (1.2 g, 70%) was obtained as an orange foam: $^1$H NMR (CDCl$_3$) δ1.36 (s, 3H), 1.44–1.74 (m, 8H), 3.49 (t, J=4.4 Hz, 1H), 3.83 (br s, 1H), 6.75 (d, J=8.0 Hz, 1H), 7.26 (d, J=1.9 Hz, 1H), 7.32 (dd, J=8.0, 1.9 Hz, 1H), 7.53 (dd, J=8.0, 8.0 Hz, 1H), 7.86 (d, J=7.8 Hz, 1H), 8.08 (dd, J=8.0, 2.0 Hz, 1H), 8.39 (dd, J=2.0, 2.0 Hz, 1H); $^{13}$C-NMR (CDCl$_3$) δ21.27, 21.71 (t), 23.87 (q), 27.76, 35.29 (t), 43.06 (s), 66.46 (d), 110.41, 120.57, 120.83, 121.24, 126.55 (d), 129.26 (s), 129.68, 132.55 (d), 140.66, 143.86, 148.95, 150.51 (s); MS (EI) m/z 309 (M+H)$^+$.

EXAMPLE 7

1,2-Dihydro-2-methyl-5-(3-nitro-phenyl)spiro[cyclohexane-1,3-[3H]indole]

5-Bromo-1,2-dihydro-2-methylspiro[cyclohexane-1,3-[3H]indole]

Using the conditions given in Example 1 the subtitled compound was prepared from 4-bromo-phenyl hydrazine HCl (3.5 g, 15.7 mmol) and cyclohexyl methyl ketone (2.0 g, 15.7 mmol). The pure material (3.0 g, 68%) was obtained as an oil: $^1$H NMR (CDCl$_3$) δ1.09 (d, J=6.5 Hz, 3H), 1.25–1.73 (m, 10H), 3.45 (br s, 1H), 3.71 (q, J=6.5 Hz, 1H), 6.47 (d, J=8.2 Hz, 1H), 7.09, dd, J=8.2, 2.0 Hz, 1H), 7.19 (d, J=2.0 Hz, 1H); $^{13}$C-NMR (CDCl$_3$) δ17.22 (q), 23.19, 23.44, 26.16, 30.17, 36.70 (t), 47.99 (s), 62.34 (d), 110.08 (s), 111.07, 126.83, 130.08 (d), 139.98, 148.49 (s); MS (EI) m/z 280,282 (M+H)$^+$.

Using the standard coupling conditions given in Example 1 the title compound was prepared from 5-bromo-1,2-dihydro-2-methylspiro[cyclohexane-1,3-[3H]indole] (0.5 g, 1.65 mmol), tetrakis(triphenylphosphine) palladium (0.08 g, 0.07 mmol) in dimethoxy-ethane (5 mL) with 3-nitrophenylboronic acid (0.33 g, 1.98 mmol) and sodium carbonate (0.53 g, 4.95 mmol) in 5 mL water. The pure material (0.35 g, 55%) was obtained as an orange brown semi-solid: $^1$H NMR (CDCl$_3$) δ1.16 (d, J=6.4 Hz, 3H), 1.38–1.83 (m, 10H), 3.7 (br s, 1H), 3.8 (q, J=6.4 Hz, 1H), 6.69 (d, J=8.0 Hz, 1H), 7.31 (dd, J=8.0, 1.8 Hz, 1H), 7.53 (dd, J=8.0, 8.0 Hz, 1H), 7.86 (d, J=7.3 Hz, 1H), 8.09 (d, J=8.0 Hz, 1H), 8.39 (dd, J=1.9, 1.9 Hz, 1H); $^{13}$C-NMR (CDCl$_3$) δ17.45 (q), 23.32, 23.70, 26.21, 30.31, 37.07 (t), 47.77 (s), 62.11 (d), 109.81, 120.78, 121.23, 122.40, 126.92 (d), 128.96 (s), 129.66, 132.51 (d), 138.63, 143.92, 148.94, 150.1 (s); MS (EI) m/z 322 (M)$^+$.

EXAMPLE 8

3,3-Dimethyl-5-(3-nitro-phenyl)-2,3-dihydro-1H-indole (WAY-160655)

3,3-dimethyl-1,3-dihydro-2H-indol-2-one

This compound was prepared using the general method described by A. Kende, Synth. Commun., 1: 12 (1982). The crude material was purified by column chromatography (SiO$_2$, methylenechloride:hexane 1:3) to afford the subtitled compound which was consistent with the reported spectral data.

The above oxindole (0.65 g, 4.03 mmol) and sodium acetate (0.334 g, 4.07 mmol) were stirred in acetic acid (5.0 mL). Bromine (0.66 g, 0.00413 mol) in acetic acid (5.0 mL) was added drop-wise to the reaction mixture. The reaction was stirred for 50 minutes, and then poured into water (10 mL). The mixture was made basic with sodium carbonate, extracted with ethyl acetate, dried (MgSO$_4$), filtered, and evaporated to give 5-bromo-1,3-dihydro-3,3-dimethyl-2H-indol-2-one (0.89 g, 92%): $^1$H NMR (DMSO-d$_6$) 1.21 (s, 6H), 6.76 (d, J=8.22 Hz, 1H), 7.29 (dd, J=2.1, 8.2 Hz, 1H), 7.49 (d, J=2.0 Hz, 1H), 10.4 (s, 1H).

To a solution of the 5-bromo-1,3-dihydro-3,3-dimethyl-2H-indol-2-one (0.9 g, 3.7 mmol) in 20 mL THF at 0° C. was added a borane-methylsulfide complex (2M in THF, 38 mL, 75 mmol). The reaction mixture was warmed to room temperature then brought to reflux for 4 hours. The mixture was cooled to room temperature and poured into H$_2$O/CH$_2$Cl$_2$ and washed with 5% NaHCO$_3$. The organic layer was washed with brine, dried (Na$_2$SO$_4$) and concentrated. The crude product was extracted in MeOH, trimethylamine N-oxide (2.0 g, 26.6 mmol) was added, and the solution was brought to reflux for 2 hours. The reaction mixture was cooled, concentrated and the crude residue purified by column chromatography (SiO$_2$, methylene chloride) to afford 5-bromo-3,3-dimethyl-2,3-dihydro-1H-indole (0.074 g, 87%) as a yellow oil: $^1$H NMR (CDCl$_3$) δ1.29 (s, 6H), 3.30 (s, 2H), 3.5 (br s, 1H), 6.49 (d, J=8.8 Hz, 1H), 7.08–7.12 (m, 2H); $^{13}$C-NMR (CDCl$_3$) δ27.69 (q), 42.21 (s), 62.01 (d), 110.38 (s), 111.09, 125.46, 130.09 (d), 141.03, 149.52 (s); MS (EI) m/z 225, 227 (M)+.

Using the standard coupling conditions given in Example 1, the title compound was prepared from 5-bromo-3,3-dimethyl-2,3-dihydro-1H-indole (0.25 g, 1.1 mmol), tetrakis (triphenylphosphine) palladium (0.08 g, 0.07 mmol) in dimethoxyethane (5 mL) with 3-nitrophenylboronic acid (0.22 g, 1.3 mmol) and sodium carbonate (0.35 g, 3.3 mmol) in 5 mL water. The title compound (0.17 g, 60%) was obtained as a brown semi-solid: $^1$H NMR (CDCl$_3$) δ1.38 (s, 3H), 3.40 (s, 2H), 6.72 (d, J=8.0 Hz, 1H), 7.29–7.34 (m, 2H), 7.54 (dd, J=8.0, 8.0 Hz, 1H), 7.86 (d, J=7.8 Hz, 1H), 8.09 (dd, J=8.0, 1.5 Hz, 1H), 8.40 (dd, J=2.0, 2.0 Hz, 1H); $^{13}$C-NMR (CDCl$_3$) δ27.89 (q), 41.93 (s), 62.05 (d), 109.78, 120.87, 121.02, 121.23, 126.87 (d), 129.19 (s), 129.69, 132.52 (d), 139.64, 143.75, 148.94, 151.17 (s); MS (EI) m/z 268 (M)+.

EXAMPLE 9

5'-(3-Chlorophenyl)-1',2'-dihydrospiro[cyclohexane-1,3'-[3H]indole]

Spiro[cyclohexane-1,3'-[3H]indol]-2'-(1'H) one

A solution of the oxindole (25g, 190 mmol) in 800 mL of anhydrous THF was cooled to −20° C., n-butyllithium (2.5M in hexanes, 152 mL, 0.38 mol) slowly added, followed by the addition of N,N,N',N'-tetramethylenediamine (51 mL, 0.38 mol,). After 15 minutes, 1,5-diiodopentane (174g, 0.54 mol) was added slowly and the mixture was allowed to warm to room temperature. After stirring for 16 hours saturated aqueous ammonium chloride solution (1 L) and ethylacetate (1 L) were added. After 15 minutes, the layers were separated and the aqueous phase was extracted with ethyl acetate. The combined organic layers were extracted with hydrochloric acid (1N, 500 mL), then washed with brine, dried (MgSO$_4$), and concentrated to obtain an oil. The oil was triturated with hexane (200 mL) and benzene (20 mL). The precipitate was collected and dried in vacuo to provide Spiro [cyclohexane-1,3'-[3H]indol]-2'-(1'H) one (26.3g, 69.6%) as colorless crystals: mp 110–114°; $^1$H NMR (DMSO-d$_6$) δ1.67 (m, 10H), 6.84 (d, 1H, J=8 Hz), 6.94 (t, 1H, J=8 Hz), 7.17 (t, 1H, J=8 Hz), 7.44 (d, 1H, J=8 Hz), 10.3 (s, 1H).

To a solution of the above oxindole (17.6 g, 90.0 mmol) in acetic acid (300 mL) was added sodium acetate (8.0 g, 100.0 mmol) and bromine (14.6 g, 91.0 mmol) with stirring. After 30 minutes at room temperature, the reaction mixture was partitioned between water and ethylacetate. The aqueous phase was extracted with ethylacetate. The combined organic layers were washed with water, dried (MgSO$_4$) and evaporated. The residue was triturated with hexane. The precipitate was collected, and dried in vacuo to provide 5-Bromo-spiro[cyclohexane-1,3'-[3H]indol]-2'(1'H)-one (16.5g, 67%) as off-white crystals: m.p. 196–199°; $^1$H NMR (DMSO-d$_6$) δ1.62 (m, 10H), 6.8 (d, 1H, J=6.8 Hz), 7.36 (d, 1H, J=8.2, 1.8 Hz), 7.58 (dd, 1H, J=8.2, 1.8 Hz), 10.44 (s, 1H).

Using the standard coupling conditions given in Example 1, the title compound was prepared from the above bromo-oxindole (0.32 g, 1.14 mmol) tetrakis(triphenylphosphine) palladium (0.08 g, 0.07 mmol) and 3-chlorophenylboronic acid (0.21 g, 1.37 mmol), and sodium carbonate (0.36 g, 3.4 mmol) in water (3 mL). 5-(3-chlorophenyl)-spiro [cyclohexane-1,3'-[3H]indol]-2(1H) -one (0.28 g, 80%) was obtained as a yellow solid: m.p. 164–165°; $^1$H NMR (CDCl$_3$) δ1.60–1.78 (m, 6H), 1.81–1.99 (m, 4H), 7.04 (d, J=8.1 Hz, 1H), 7.22–7.47 (m, 4H), 7.53 (s, 1H), 7.61 (s, 1H), 9.28 (br s, 1H); $^{13}$C-NMR (CDCl$_3$) δ20.17, 24.12, 31.92 (t), 47.22 (s), 109.21, 121.94, 124.06, 125.50,125.79,125.97, 126.38, 128.96 (d), 132.88, 133.59, 135.60, 139.14, 142.17, 182.89 (s); MS (EI) m/z 310, 312 (M−H)+.

To a solution of 5-(3-chlorophenyl)-spiro[cyclohexane-1,3-[3H]indol]-2(1H)-one (0.42 g, 1.4 mmol) in 20 mL THF at 0° C. is added borane-dimethylsulfide complex, (2M in THF, 14 mL, 28 mmol). The reaction mixture was warmed to room temperature then brought to reflux for 4 hours The mixture was cooled to room temperature and poured into H$_2$O with CH$_2$Cl$_2$ and washed with 5% NaHCO$_3$. The organic layer was washed with brine, dried over Na$_2$SO$_4$ and concentrated. The crude product was extracted in MeOH and trimethylamine N-oxide (1.0 g, 9.0 mmol) was added. The solution was brought to reflux for 2 hours, the mixture was cooled, concentrated and the crude residue purified by column chromatography (SiO$_2$, methylene chloride) to afford the title compound (0.25 g, 63%) as a yellow oil: $^1$H NMR (CDCl$_3$) δ1.3–1.55 (m, 3H), 1.6–1.85 (m, 7H), 3.1 (br s, 1H). 3.5 (s, 2H), 6.6 (d, J=8.0 Hz, 1H), 7.18–7.32 (m, 4H), 7.4 (dd, J=7.7, 1.5 Hz, 1H), 7.5 (s, 1H); $^{13}$C-NMR (CDCl$_3$) δ23.65, 26.24, 37.00 (t), 46.58 (s), 57.49 (t), 109.95, 121.82, 125.07, 126.36, 126.98, 127.08, 130.29 (d), 130.64, 134.91, 139.65, 144.29, 151.09 (s); MS (EI) m/z 298, 300 (M+H)+.

EXAMPLE 10

3-(2',3',3'-trimethyl-2',3-dihydro-1H-indol -5'-yl) benzonitrile

To a solution of 5-bromo-2,3,3-trimethyl-2,3-dihydro-1H-indole (2.03 g, 8.45 mmol) in dimethoxyethane (50 mL), under nitrogen was added tetrakis(triphenylphosphine) palladium (0.47 g, 0.4 mmol). After 20 minutes at room temperature, 3-formylphenylboronic acid (2.36 g, 16.4 mmol) and potassium carbonate (6.80 g, 55 mmol) in water (25 mL) was added, and the mixture was heated under reflux. After 2 hours, the mixture was cooled, poured into brine and extracted with EtOAc (×2). The combined organic extracts were washed with brine, dried (MgSO$_4$) and evaporated. The residue was then subjected to column chromatography (SiO$_2$, EtOAc:hexane, 1:8) to afford 3-(2',3,3'-trimethyl-2',3-dihydro-1H-indol-5'-yl) benzaldehyde (0.96 g, 3.62 mmol, 43%) as a slightly impure solid that was used without further purification: $^1$H NMR (CDCl$_3$) δ1.11 (s, 3H), 1.22 (d, 3H, J=6.5 Hz), 1.35 (s, 3H), 3.59 (dd, 1H, J=13, 7 Hz), 6.69 (d, 1H, J=1 Hz), 7.25 (s, 1H), 7.32 (s, 1H), 7.55 (t, 1H, J=7.6 Hz), 7.80 (d, 1H, J=1 Hz), 7.82 (d, 1H, J=1Hz), 8.05 (s, 1H), 10.07 (s, 1H).

To a solution of the above compound (0.96 g, 3.62 mmol) in MeCN/H$_2$O (20 mL, 95:5) was added hydroxylamine hydrochloride (0.82 g, 7.25 mmol). After 1 hour, the mixture was poured into a saturated sodium hydrogen carbonate solution and extracted with EtOAc (×2). The combined organic extracts were washed with water, dried (MgSO$_4$) and evaporated. The residue was then dissolved in dichloromethane (20 mL) and treated with thionyl chloride (0.53 mL, 7.25 mmol). After 16 hours, the mixture was quenched with saturated sodium hydrogen carbonate solution and concentrated, partitioned between water and EtOAc, and re-extracted with EtOAc. The combined organic extracts were washed with brine, dried (MgSO$_4$) and evaporated. Purification by column chromatography (EtOAc: hexane, 1:8) afforded a yellow oil (0.31 g) which was dissolved in methanol (5 mL) and treated with ethereal hydrogen chloride (1 M, 1.3 mL, 1.3 mmol) and evaporated. Recrystallization from MeOH/Et$_2$O then afforded the title compound (0.20 g, 0.60 mmol, 18%): mp>235° C. (decomp), $^1$H NMR (CDCl$_3$) δ1.57 (s, 3H), 1.36 (d, 3H, J=6.7 Hz), 1.40 (s, 3H),3.72–3.76 (m, 1H), 7.30 (d, 1H, J=8 Hz), 7.67 (t, 2H, J=7 Hz), 7.79–7.84 (m, 2H), 8.03 (d, 1H, J=8 Hz), (8.2, s, 1H); MS (EI) m/z 262 (M)$^+$.

EXAMPLE 11

Pharmacology

The biological activity for the compounds of the current invention was evaluated in the in-vitro and in-vivo assays described below. In-vitro potencies lie in the range 0.01 nM–10,000 nM, and in-vivo potencies in the range 1 μg/kg to 100 mg/kg.

A. In-vitro Biology

The in-vitro biology is determined by (1) competitive radioligand Binding: using the A-form of the human progesterone receptor with progesterone as the radioligand; (2) co-transfection assay, which provides functional activity expressed as agonist EC50 and Antagonist IC50 values; and (3) a T47D cell proliferation, which is a further functional assay which also provides agonist and antagonist data. 1. hPR Binding Assay This assay is carried out in accordance with: Pathirana, C.; Stein, R. B.; Berger, T. S.; Fenical, W.; Ianiro, T.; Mais, D. E.; Torres, A.; Glodman, M. E., Nonsteroidal human progesterone receptor modulators from the marine alga cymoplia barbata, J. Steroid Biochem. Mol. Biol., 1992, 41, 733–738.

2. PRE-luciferase Assay in CV-1 cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium

The growth medium was as follows: DMEM (BioWhittaker) containing 10% (v/v) fetal bovine serum (heat inactivated), 0.1 mM MEM non-essential amino acids, 100 U/ml penicillin, 100 mg/mg streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment and Luciferase Assay

Stock CV-1 cells are maintained in growth medium. Co-transfection is done using 1.2×10$^7$ cells, 5 mg pLEM plasmid with hPR-B inserted at Sph1 and BamH1 sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliers. EC$_{50}$ or IC$_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in full dose-response curves and the EC$_{50}$ or IC$_{50}$ values are calculated.

TABLE 1

Estimated EC$_{50}$, standard error (SE), and 95% confidence intervals (CI) for reference progestins from three individual studies

| Compound | Exp. | EC$_{50}$ (nM) | SE | 95% CI lower | 95% CI upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 2

Estimated IC$_{50}$, standard error (SE), and 95% confident interval (CI) for the antiprogestin, RU486 from three individual studies

| Compound | Exp. | IC$_{50}$ (nM) | SE | 95% CI lower | 95% CI upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

EC$_{50}$: Concentration of a compound that gives half-maximal increase PRE-luciferase activity (default-nM) with SE.

IC$_{50}$: Concentration of a compound that gives half-maximal decrease in 3 nM progesterone induced PRE-luciferase activity (default-nM) with SE.

3. T47D Cell Proliferation Assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth Medium

DMEM:F12 (1:1) (GIBCO, BRL) supplemented with 10% (v/v) fetal bovine serum (not heat-inactivated), 100 U/ml penicillin, 100 mg/ml streptomycin, and 2 mM GlutaMax (GIBCO, BRL).

b. Treatment Medium

Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell Culture

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in full dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min, followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 μl of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 3

Estimated $EC_{50}$, standard error (SE), and 95% confidence intervals (CI) for individual studies

| Compound | Exp | $EC_{50}$ (nM) | SE | 95% CI lower | 95% CI upper |
| --- | --- | --- | --- | --- | --- |
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.001 | 0.011 | 0.024 |

TABLE 4

Estimated $IC_{50}$, standard error, and 95% confident interval for the antiprogestin, RU486

| Compound | Exp | $IC_{50}$ (nM) | SE | 95% CI lower | 95% CI upper |
| --- | --- | --- | --- | --- | --- |
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE.

All above-noted published references are incorporated herein by reference. Numerous modification and variations of the present invention are included in the above-identified specification are expected to be obvious to one of skill in the art. Such modifications and alterations to the methods, solutions, apparatuses of the present invention are believed to be encompassed in the scope of the claims appended hereto.

What is claimed:

1. A compound of the formula:

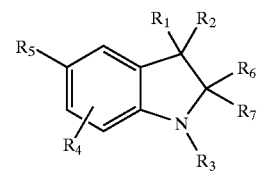

I wherein:
$R_1$ and $R_2$ are selected independently from the group consisting of H, alkyl, substituted alkyl, OH, O(alkyl), O(substituted alkyl), O(Acetyl), aryl, substituted aryl, heteroaryl, substituted heteroaryl, alkylaryl, alkylheteroaryl, 1-propynyl, and 3-propynyl;

$R_3$ is H, OH, $NH_2$, $C_1$ to $C_6$ alkyl, substituted $C_1$ to $C_6$ alkyl, $C_3$ to $C_6$ alkenyl, alkynyl, substituted alkynyl, or $COR^A$;

$R^A$ is H, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R_4$ is H, halogen, CN, $NH_2$, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl;

$R_5$ is selected from the group consisting of a) and b):
a) a benzene ring of the formula:

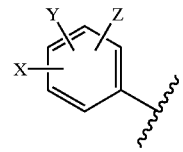

X is selected from the group consisting of halogen, OH, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, S(O)

alkyl, S(O)$_2$alkyl, C$_1$ to C$_3$ aminoalkyl, substituted C$_1$ to C$_3$ aminoalkyl, NO$_2$, C$_1$ to C$_3$ perfluoroalkyl, 5 or 6 membered heterocyclic ring having in its backbone 1 to 3 heteroatoms, COR$^B$, OCOR$^B$, and NR$^C$COR$^B$;

R$^B$ is H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;

R$^C$ is H, C$_1$ to C$_3$ alkyl, or substituted C$_1$ to C$_3$ alkyl:

Y and Z are independently selected from the group consisting of H, halogen, CN, NO$_2$, C$_1$ to C$_3$ alkoxy, C$_1$ to C$_3$ alkyl, and C$_1$ to C$_3$ thioalkyl; and b) an indol-4-yl, indol-7-yl or benzo-2-thiophene moiety, the moiety being optionally substituted by from 1 to 3 substituents selected from the group consisting of halogen, lower alkyl, CN, NO$_2$, lower alkoxy, and CF$_3$;

R$_6$ and R$_7$ are independently selected from the group consisting of H, methyl, ethyl, propyl, butyl, iso-propyl, iso-butyl, cyclohexyl, aryl, substituted aryl, heteroaryl, and substituted heteroaryl;

or pharmaceutically acceptable salt thereof.

2. The compound according to claim 1 of the formula:

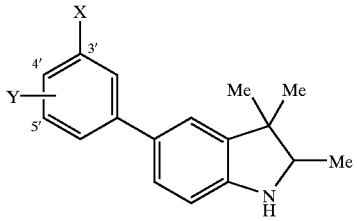

wherein:

X is selected from the group consisting of halogen, CN, C$_1$ to C$_3$ alkoxy, C$_1$ to C$_3$ alkyl, NO$_2$, C$_1$ to C$_3$ perfluoroalkyl, 5-membered heterocyclic ring having in its backbone 1 to 3 heteroatoms, and C$_1$ to C$_3$ thioalkoxy;

Y is on the 4' or 5' position and is selected from the group consisting of H, halogen, CN, NO$_2$, C$_1$ to C$_3$ alkoxy, C$_1$ to C$_3$ alkyl, and C$_1$ to C$_3$ thioalkyl.

3. The compound according to claim 2 wherein X is CN or NO$_2$ and Y is 5'-fluoro.

4. The compound according to claim 1 which is 2,3,3-Trimethyl-5-(3-nitro-phenyl)-2,3-dihydro-1H-indole or a pharmaceutically acceptable salt thereof.

5. The compound according to claim 1 which is 2,3,3-Trimethyl-5-(3-nitro-phenyl)-2,3-dihydro-1H-indole Hydrochloride or a pharmaceutically acceptable salt thereof.

6. The compound according to claim 1 which is (2-R)-2,3,3-Trimethyl-5-(3-nitro-phenyl)-2,3-dihydro-1H-indole or a pharmaceutically acceptable salt thereof.

7. The compound according to claim 1 which is (2-S)-2,3,3-Trimethyl-5-(3-nitro-phenyl)-2,3-dihydro-1H-indole or a pharmaceutically acceptable salt thereof.

8. The compound according to claim 1 which is 2,3,3-Diethyl-2-methyl-5-(3-nitro-phenyl)-2,3-dihydro-1H-indole or a pharmaceutically acceptable salt thereof.

9. The compound according to claim 1 which is 3,3-Dimethyl-5-(3-nitro-phenyl)-2,3-dihydro-1H-indole or a pharmaceutically acceptable salt thereof.

10. The compound according to claim 1 which is 3-(2',3',3'-trimethyl-2',3-dihydro-1H-indol-5'-yl) benzonitrile or a pharmaceutically acceptable salt thereof.

11. A pharmaceutical composition comprising a pharmaceutically effective amount of a compound of claim 1 and a pharmaceutically acceptable carrier or excipient.

12. A method of inducing contraception in a mammal, the method comprising administering to the mammal a pharmaceutically effective amount of a compound of claim 1, or a pharmaceutically acceptable salt thereof.

13. A compound of the formula:

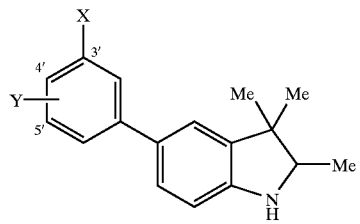

wherein:

X is selected from the group consisting of halogen, CN, C$_1$ to C$_3$ alkoxy, C$_1$ to C$_3$ alkyl, NO$_2$, C$_1$ to C$_3$ perfluoroalkyl, 5-membered heterocyclic ring containing in its backbone 1 to 3 heteroatoms, and C$_1$ to C$_3$ thioalkoxy;

Y is on the 4' or 5' position and is selected from the group consisting of H, halogen, CN, NO$_2$, C$_1$ to C$_3$ alkoxy, C$_1$ to C$_4$ alkyl, and C$_1$ to C$_3$ thioalkyl;

or pharmaceutically acceptable salt thereof.

14. A pharmaceutical composition comprising a pharmaceutically effective amount of a compound of claim 13 and a pharmaceutically acceptable carrier or excipient.

15. A method of inducing contraception in a mammal, the method comprising administering to the mammal a pharmaceutically effective amount of a compound of claim 13, or a pharmaceutically acceptable salt thereof.

* * * * *

UNITED STATES PATENT AND TRADEMARK OFFICE
CERTIFICATE OF CORRECTION

PATENT NO.  : 6,417,214 B1
DATED       : July 9, 2002
INVENTOR(S) : John W. Ullrich et al.

It is certified that error appears in the above-identified patent and that said Letters Patent is hereby corrected as shown below:

<u>Title page,</u>
Under FOREIGN PATENT DOCUMENTS, replace "WO 98/27069" with -- WO 98/27059 --.

<u>Column 11,</u>
Lines 7-12, replace the following structure:

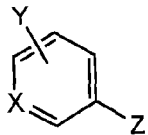

with the following structure:

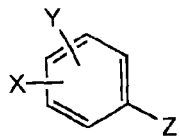

<u>Column 12,</u>
Lines 25-30, replace the following structure:

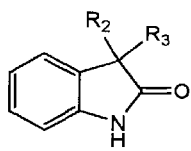

with the following structure:

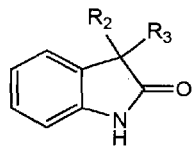

$R_2 = R_3 = -(CH_2)_n-$

UNITED STATES PATENT AND TRADEMARK OFFICE
CERTIFICATE OF CORRECTION

PATENT NO.    : 6,417,214 B1
DATED         : July 9, 2002
INVENTOR(S)   : John W. Ullrich et al.

It is certified that error appears in the above-identified patent and that said Letters Patent is hereby corrected as shown below:

Column 12 cont'd,
Line 35, replace "TFA-N-oxide" with -- TEA-N-oxide --.

Column 14,
Line 32, replace "6;" with -- δ; --.

Column 19,
Line 39, replace "100 mg/mg" with -- mg/ml --.

Signed and Sealed this

Twenty-eighth Day of January, 2003

JAMES E. ROGAN
*Director of the United States Patent and Trademark Office*